(12) United States Patent
Bostrom et al.

(10) Patent No.: US 8,109,133 B2
(45) Date of Patent: Feb. 7, 2012

(54) METHOD AND DEVICE FOR MEASURING LIQUID ABSORPTION

(75) Inventors: Bernt Bostrom, Hagersten (SE); Ulf Backlund, Stockholm (SE)

(73) Assignee: Fibro System AB, Stockholm (SE)

( * ) Notice: Subject to any disclaimer, the term of this patent is extended or adjusted under 35 U.S.C. 154(b) by 350 days.

(21) Appl. No.: 12/310,989

(22) PCT Filed: Sep. 12, 2007

(86) PCT No.: PCT/SE2007/000793
§ 371 (c)(1),
(2), (4) Date: Mar. 12, 2009

(87) PCT Pub. No.: WO2008/033074
PCT Pub. Date: Mar. 20, 2008

(65) Prior Publication Data
US 2009/0199624 A1    Aug. 13, 2009

(30) Foreign Application Priority Data
Sep. 15, 2006   (SE) ...................................... 0601908

(51) Int. Cl.
*G01N 5/02*     (2006.01)
*G01N 25/56*    (2006.01)

(52) U.S. Cl. ............................................................ 73/73
(58) Field of Classification Search ....................... 73/73
See application file for complete search history.

(56) References Cited

U.S. PATENT DOCUMENTS

| | | | |
|---|---|---|---|
| 3,952,584 A | * | 4/1976 | Lichstein ......................... 73/73 |
| 4,976,138 A | | 12/1990 | Benninghoff et al. |
| 5,138,870 A | | 8/1992 | Lyssy |

* cited by examiner

*Primary Examiner* — Lisa Caputo
*Assistant Examiner* — Roger Hernandez-Prewitt
(74) *Attorney, Agent, or Firm* — Mark P. Stone

(57) ABSTRACT

The invention concerns a method and a device for measuring the ability of a material to absorb a liquid, whereby a liquid is brought into contact with a surface of a test specimen (P) of the material, and wherein the amount of liquid that has been absorbed in the test specimen is calculated. A certain amount of liquid is supplied to a liquid chamber unit, which on one side is limited by said surface, such that an amount of liquid which is absorbed by the test specimen leaves the liquid chamber unit and a representation comprising an indication of the reduction of the amount of liquid in the liquid chamber unit is produced.

18 Claims, 3 Drawing Sheets

METHOD AND DEVICE FOR MEASURING LIQUID ABSORPTION

FIELD OF THE INVENTION

The invention concerns a method and a device according to the preambles of the respective independent claims.

BACKGROUND OF THE INVENTION

The ability of paper or cardboard absorb water is an important property in order to determine the suitability of the paper or cardboard for different fields of use. The "Cobb value" of a paper is a measure of this ability to absorb water.

From a general point of view the Cobb method is carried out such that an area of 100 cm$^2$ of a paper specimen during 60 seconds is subjected to influence from water, whereafter excess water is removed in a prescribed manner. Starting out from the weight of the paper before and after the exposure, the weight of the absorbed water is determined, which gives the Cobb value. A high Cobb value thus means that the water absorption ability is high and a low Cobb value that the water absorption ability is low.

The Cobb method (ISO 535) is a manual method which is slow, uncertain and labour-intensive and therefore costly. Because of the manual elements in the method, high accuracy on the side of the operator carrying out the method is required in order to avoid important erroneous measurements and thereby basically wrongful determinations of the ability of the paper to absorb water.

The Aim and most Important Features of the Invention

It is an aim of the present invention to provide a method and a device as mentioned above that eliminates the problem of the previously known manual method. In particular the invention aims to provide a secure, fast and economic method and a device which overcomes these problems.

These aims are obtained in respect of a method and a device as mentioned initially through the characterizing features of the independent claims.

Hereby is achieved that the change in the amount of liquid in the liquid chamber unit is used for calculating the amount of liquid that is absorbed in the material specimen. Manual sources of errors such as erroneously supplied amount of liquid, erroneously executed blotting etc. can be directly eliminated through the invention. In addition it is possible to automate the method. The time period thereof is then essentially only controlled by the time when the liquid is in contact with the surface of the specimen.

The invention is firstly intended for different types of measurements of the ability of paper to absorb not only water but also other liquids such as oils, solvents, impregnating agents etc.

The invention is also applicable for measurements on other surfaces, besides papers, such as plastics, textiles, wooden materials, surface coverings etc. for determining the ability of these materials to absorb different liquids.

In particular, and which is preferred, the liquid-contacting surface of the test specimen is brought to lie against one side of a rigid and water permeable wall of a main chamber of the liquid chamber unit. Hereby is avoided that possible wrinkling and other undesired movements of the test specimen affect the measuring results. in an erroneous direction. In particular it is preferred that the test specimen is pressed against said wall, for example by means of a flexible membrane or any other elastic means in order to further ensure the flatness of the test specimen and avoid movements of the test specimen during the measurement, inducing sources of errors.

In a preferred embodiment, the liquid chamber unit is connected to a sensor chamber wherein the liquid level is sensed. By forming the sensor chamber with an essentially smaller surface area than the surface area, with which the liquid contacts the material specimen, an amplified level change in the sensor chamber is achieved during the process of the measurement, also in case of relatively low liquid absorption, which increases the precision in the measurement.

By the test specimen being sealingly clamped against a housing portion including the liquid chamber unit, leakage as a source of errors is prevented.

Corresponding advantages are obtained with the corresponding features of a device for measuring according to the invention.

BRIEF DESCRIPTION OF DRAWINGS

The invention will now be described in greater detail by way of embodiments and with reference to the enclosed drawings, wherein.

DESCRIPTION OF EMBODIMENTS

Figure 1:
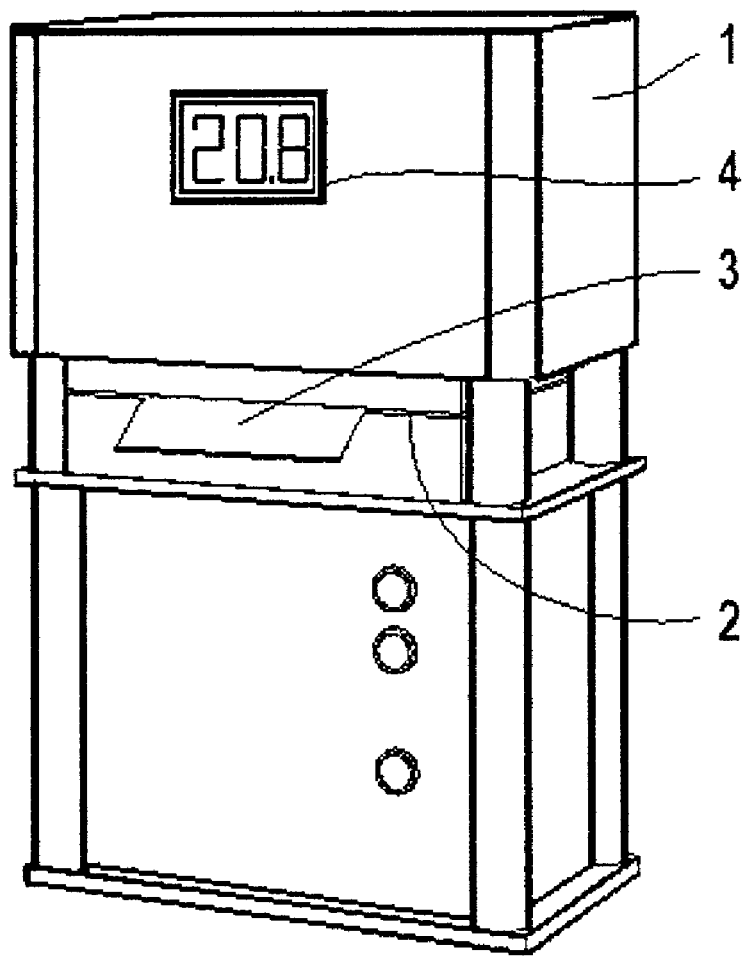
FIG. 1 shows a device for measuring liquid absorption ability of a material.

The device indicated with 1 in FIG. 1 for measuring the liquid absorption ability of a material includes a housing, a slot 2 for the insertion of a test specimen in the form of e.g. a paper sheet 3 to be.tested, and a display 4 for displaying a measured Cobb value. Manoeuvring means and lamps for indication of the status of the device are arranged on the front side of the housing. The device has further (not shown) means for supplying liquid to be used for the measurement.

Figure 2A:
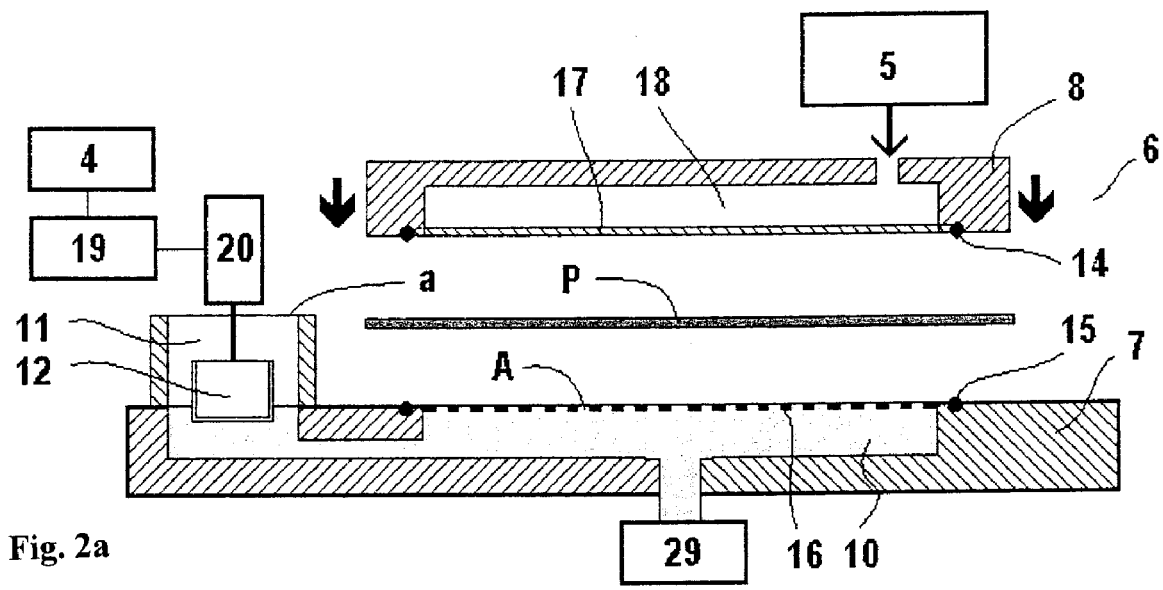
FIGS. 2a and 2b show a section through a control chamber unit with adjacent components according to a first embodiment of the invention in two different positions.

FIG. 2a shows diagrammatically in an enlarged section, with some elements left out for clarity, a measuring unit of a device for measuring the ability of a material to absorb a liquid. The measuring housing, generally indicated with 6, includes a first housing portion 7 and a second housing portion 8 which are mutually displaceable with respect to each other from the position shown in FIG. 2a. In this position there exists a distance between the first and the second housing portions in order to admit the introduction of a test specimen P, for example a sheet of paper to be tested, between the housing portions.

Figure 2B:
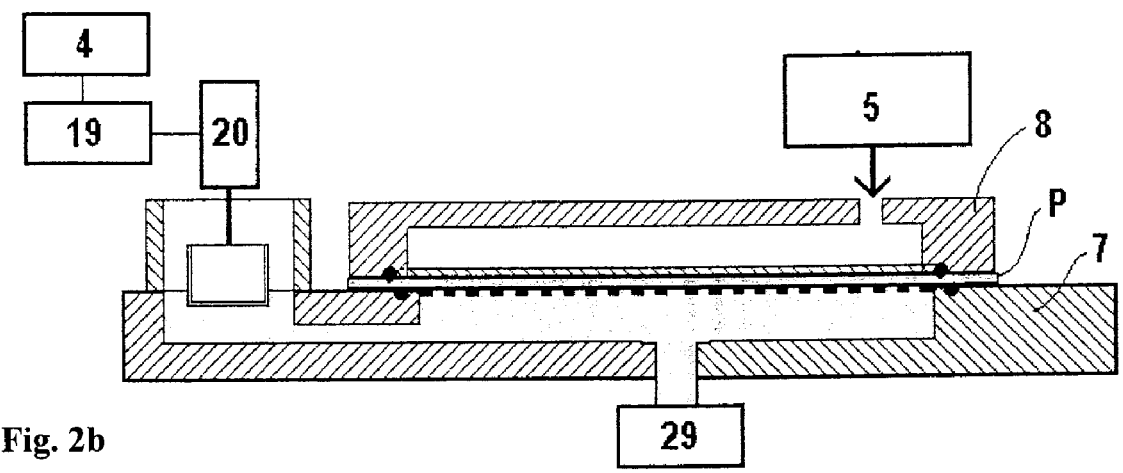

From said position, the housing portions are moveable relative to each other into a position shown in FIG. 2b, wherein the housing portions, with the aid of sealings 14, 15, sealingly clamp around a test area of a predetermined size of the test specimen P.

The first housing portion 7 contains a liquid chamber unit, which includes a main chamber 10 for contacting said area of the test specimen P during the measuring process. The main chamber 10 is connected to a sensor chamber 11 which includes a floater 12 being connected to a sensor 20. The sensor chamber 11 is constructed such that liquid is supplied to a certain pre-determined level when the main chamber 10 is filled by means of a connected pump 29 and cavities in the liquid-permeable wall 16 (see below) are filled. The sensor chamber 11 can be part of or be connected to the liquid chamber unit. Reference 16 indicates a rigid liquid-permeable wall, which is (essentially) flat and the purpose of which being to prevent the test specimen from assuming a shape during wetting, which could result in an erroneous measurement.

The second housing portion 8 includes a pressing means 17 in the form of a flexible wall, for example such as a rubber membrane, which during the measuring process exerts a certain pressure onto the back side of the test specimen P such that this is gently pressed against the rigid liquid-permeable wall. 16 in order to further ensure that erroneous measurements, because of deformation of the test specimen P during wetting, does not occur.

An air chamber 18 can be pressurized with a gentle pressure for ensuring that the pressing means 17 in a prescribed manner is pressed against the liquid-permeable wall 16 through a pressure regulator 5.

The sensor chamber 11 has a surface area "a", as seen transversally, which is preferably essentially smaller than the testing area "A" of the main chamber 10, whereby also a relatively small liquid absorption by a test specimen P during the measuring process results in a relatively great level change in the sensor chamber 11 depending on the relationship A/a. This level change is sensed by a. sensor 20 which transmits signals to a computing unit (CPU) 19, which transforms the signal to a visually readable value, for example a Cobb value, which is shown on the display 4.

Figure 4:
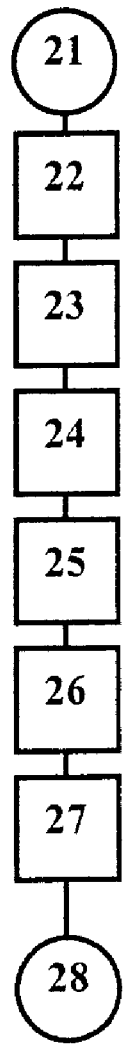
FIG. 4 shows a block diagram over a method according to the invention.

A method sequence will now be described with reference to FIG. 4, wherein:

Position 21 indicates the start of the sequence with preparing for operation with supply of liquid into the liquid chamber unit, such that liquid is filled into the main chamber and the sensor chamber and also cavities, pores or the like in the liquid-permeable wall in order to ensure that the liquid will securely come into contact with the test specimen P over the entire test surface A. Liquid is supplied with a certain volume to the desired level, whereupon filling is terminated.

Position 22 indicates loading of a test specimen in the form of for example a sheet of paper to be tested.

Position 23 indicates the start of the measuring process as soon as the housing portions have been brought together such that a sealed contact with the test specimen between them is obtained and wetting is allowed to occur during a certain determined time period, as for example is prescribed for the particular measuring method to be applied.

Position 24 indicates that the measuring period is terminated and the final liquid level in the sensor chamber is read.

Position 25 indicates transmission of a read signal from the sensor to the computing unit, which transforms the sensor signal into a value for the amount of liquid that has been absorbed by the test specimen, to be displayed on a display.

Position 26 indicates elimination of free liquid on the test surface by for example suction, blowing, blotting or a combination thereof, so that the test specimen is easier to handle for the operator after finalized measuring.

Position 27 indicates opening of the housing portions and removing of the test specimen.

Position 28 indicates flushing of the liquid chamber unit and the liquid-permeable wall with clean liquid, resetting the system and termination of the method sequence.

The invention can be varied within the scope of the following claims and be modified in different ways.

For example it is within the scope of the invention to read the liquid level change in a liquid chamber unit in any other way as for example optically with the aid of light (such as laser), by acoustic means, by electromagnetic means, a combination of at least two of these methods or by any other per se known method. The floater could also be directly connected over per se known linkage arms to a mechanical indicator which can relate to an adjustable or changeable scale over a value/a final value.

It is fully possible to envisage that in some situations, for example where no change of form of the test specimen in the direction towards or from the main chamber occurs or is expected to occur, to leave out the rigid liquid-permeable wall such that instead the test surface of the test specimen directly limits the main chamber. It is also possible, in certain situations, to eliminate the pressing means for similar reasons. These modifications are however normally not preferred.

The insertion of the test specimen can be made automatically through the operation of a motor or entirely manually. The movements of the housing portions can be controlled automatically or even be effected manually. Also a solution with stationary housing portions and influencing the test specimen with particular pressing means in order to achieve sealing contact, is within the scope of the invention.

In order to ensure improved repeatability and minimize the risk of erroneous measurements, the measurement of the embodiment according to FIG. 2a must be initiated as soon as possible after the test surface has come into contact with the test liquid.

Figure 3A:
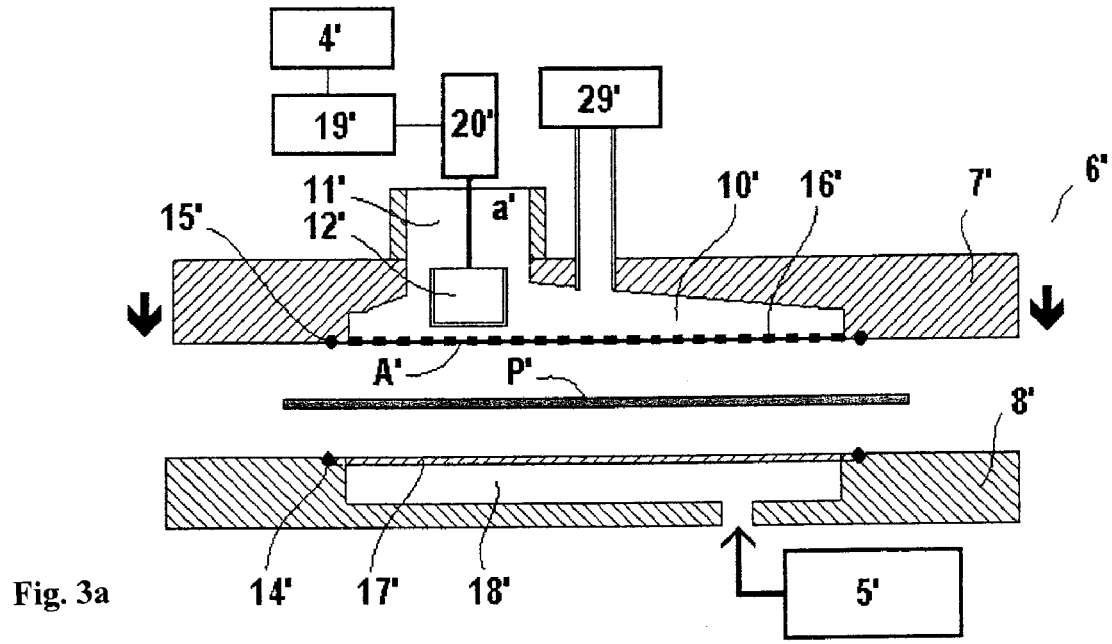
FIGS. 3a and 3b show a section through a control chamber unit with adjacent components according to a second embodiment of the invention in two different positions.
Figure 3B:
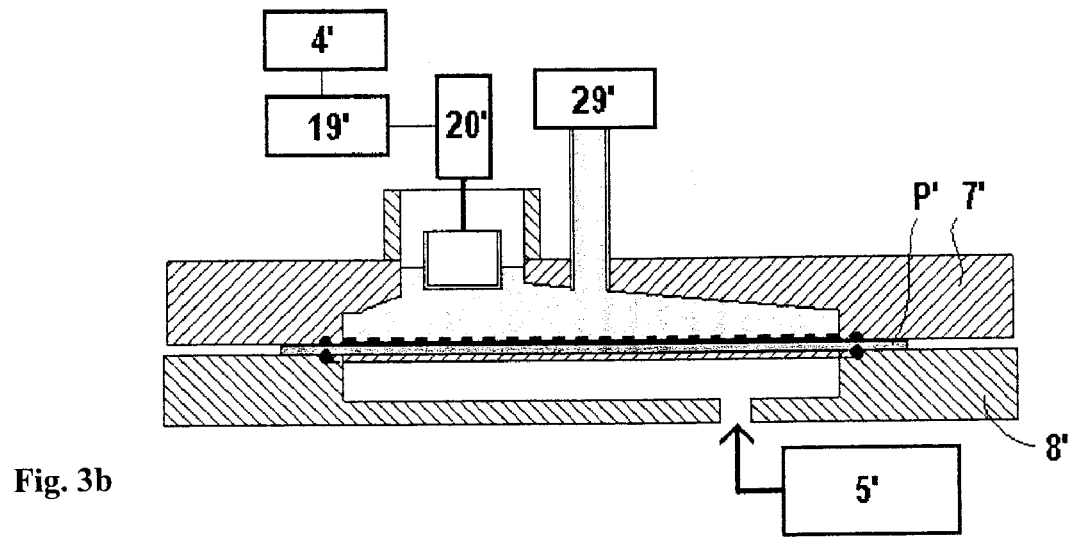

In another embodiment according to FIGS. 3a and 3b the liquid chamber is positioned above the test specimen and filled after bringing the housing portions together. In this embodiment, filling of liquid should be fast and automatic, for greater repeatability and greater security against erroneous measurements. This figure includes the reference numerals used in FIGS. 2a and 2b with a (')-sign.

From the position in FIG. 3a, the housing portions are moveable relative to each other into a position shown in FIG. 3b, wherein the housing portions with the aid of the seals 14,15 sealingly clamp around a test area of a predetermined size of the test specimen P. This procedure is analogous to what is stated for FIGS. 2a and 2b.

Emptying of the liquid chamber unit of the embodiment according to FIGS. 3a and 3b can be made in many ways. For example, emptying can be made in combination with perforating the test specimen for feeding out/sucking out through the resulting hole. Alternatively, the liquid could be sucked back through the liquid-permeable wall.

As is stated above, different measurement methods can be used for the measuring of the liquid absorption in test specimens of different kinds, even if the background of the description in general has been the Cobb method, which is an established method for measuring water absorption in different types of paper. Thus, also other materials according to the above can be applied for measuring, also in connection with other liquids than water.

In order to ensure that the liquid is not prevented by the liquid-permeable wall from coming into full contact with the test specimen, it is suggested in a modified variant of the embodiment in FIGS. 3a and 3b that, in connection with filling liquid, a certain amount is brought in between the liquid-permeable wall and test specimen. This can be achieved for example by introducing a spraying device, which in connection with the test specimen being somewhat separated from the liquid-permeable wall, for example starting out from a central position of the wall, sprays the liquid sideward for total wetting of the entire specimen surface.

The liquid-permeable wall can be of different kinds, for example a fine-meshed metal net, a porous sintered material or a perforated metal foil which is stretched in the liquid chamber unit.

The specimen test surface can be oriented in other ways, for example vertically or with the main chamber positioned above the test specimen (FIG. 3a). It is not excluded that a test surface can be an edge-portion, for example the edge of a cut-out hole in a test specimen.

The invention enables accurate calibration in order to take different parameters into consideration such as for example unevenness in the liquid-permeable wall such as mesh unevenness in the case of a metal net. Also calibration at the background of prevailing temperatures. can be within the scope of the invention.

Filling of water into the liquid chamber unit can be controlled through overflow or be controlled by the sensor 20, which cuts off the water supply at a certain reference level. Also other per se known procedures can be adapted.

As an alternative to the above discussed systems it is also possible to envisage a solution wherein a liquid chamber unit has constant volume, and wherein a very accurate pump supplies a second amount of liquid in order to replace the reduction of the first amount of liquid in the liquid chamber unit corresponding to the amount of liquid being absorbed by a test specimen. A signal describing in such a way supplied liquid amount or pump action can then be used in order to obtain a measurement of absorbed liquid in a test specimen. This modification is however not preferred.

Through the invention it has become possible to calculate a prediction of the final value already after a short time of liquid influence on the test specimen since the invention allows measurements continuously, or at short intervals, of the water absorption in principle from the start of the test period. This gives the possibility to obtain a large number of measuring points already after a short time in order to, with the aid of known mathematic functions, calculate a theoretical value with for example an exponential function. This has the advantage that a reliable result can be obtained long before the end of an established test period, which means faster response, higher productivity and lower costs. In the case of a Cobb value, such a reliable result could be obtained already after for example 10-30 seconds as a contrast to the established testing time of 60 seconds.

The invention claimed is:

1. Method for measuring ability of a material to absorb liquid, wherein a liquid is brought into contact with a surface of a test specimen of the material, and wherein the amount of liquid that has been absorbed in the test specimen is calculated, wherein
   a certain first amount of liquid is supplied to a liquid chamber unit, which on one side is limited by said surface, such that an amount of liquid which is absorbed by the test specimen leaves the liquid chamber unit,
   a representation comprising an indication of the reduction of the amount of liquid in the liquid chamber unit is produced, and
   said surface of the test specimen is brought to lie against one side of an essentially rigid liquid-permeable wall of a main chamber of the liquid chamber unit.

2. Method according to claim 1, wherein said representation comprising an indication of the reduction of the amount of liquid in the liquid chamber unit is an indication of a liquid level change In the liquid chamber unit.

3. Method according to claim 1, wherein a value denoting the liquid absorption ability of the material is calculated.

4. Method according to claim 1, wherein the test specimen is pressed against said wall.

5. Method according to claim 1, wherein a liquid level in a sensor chamber is sensed.

6. Method according to claim 1, wherein the test specimen is clamped sealingly against a housing portion.

7. Method according to claim 1, wherein said representation is produced continuously or with intervals or after the end of a certain prescribed time period.

8. Method according to claim 1, wherein a prediction value for the final value concerning the amount of liquid absorbed in the test specimen is calculated.

9. Device for measuring liquid absorption ability of a material, including means for bringing a liquid Into contact with a surface of a test specimen of the material In order to calculate the amount of liquid absorbed in the test specimen, the device further including:
   a liquid chamber unit adapted for the supply of a certain first amount of liquid, and being arranged such that it on one side will be limited by said surface, such that liquid being absorbed by the test specimen leaves the liquid chamber unit,
   measuring means for producing a representation of reduction of the amount of liquid in the liquid chamber unit, and
   the liquid chamber unit including a main chamber with a rigid liquid-preamble wall, against which said surface of the test specimen is intended to contact.

10. Device according to claim 9, wherein said measuring means for producing a representation of reduction of the amount of liquid in the liquid chamber unit are arranged to indicate a liquid level change in the liquid chamber unit.

11. Device according to claim 9, said device further including means for calculating a value denoting the liquid absorption ability of the material.

12. Device according to claim 9, said device further including a pressing means for pressing the test specimen against said wall.

13. Device according to claim 9, wherein the liquid chamber unit includes a sensor chamber, wherein a liquid level is intended to be sensed by any means from the group: a floater, an acoustic sensor, an optic sensor, an electromagnetic sensor or a combination of two or more thereof.

14. Device according to claim 9, wherein the liquid chamber unit includes a first housing portion, against which the test specimen is Intended to be sealingly clamped.

15. Device according to claim 14, wherein said device includes a second housing portion for clamping interaction against the test specimen, with the first housing portion.

16. Device according to claim 9, said device further including means for calculating a prediction of the final value concerning the amount of liquid absorbed by the test specimen.

17. Method according to claim 2, wherein a value denoting the liquid absorption ability of the material is calculated.

18. Device according to claim 10, wherein said device further includes means for calculating a value denoting the liquid absorption ability of the material.

* * * * *

UNITED STATES PATENT AND TRADEMARK OFFICE
CERTIFICATE OF CORRECTION

| | | |
|---|---|---|
| PATENT NO. | : 8,109,133 B2 | Page 1 of 1 |
| APPLICATION NO. | : 12/310989 | |
| DATED | : February 7, 2012 | |
| INVENTOR(S) | : Bernt Bostrom and Ulf Backlund | |

It is certified that error appears in the above-identified patent and that said Letters Patent is hereby corrected as shown below:

Column 6, Line 18 (Claim 9, Line 2): Delete "Into", and substitute -- into --.

Column 6, Line 19 (Claim 9, Line 3): Delete "In", and substitute -- in --.

Column 6, Line 31 (Claim 9, Line 15): Delete "preamble", and substitute -- permeable --.

Signed and Sealed this
Third Day of April, 2012

David J. Kappos
*Director of the United States Patent and Trademark Office*